United States Patent
Tang et al.

(10) Patent No.: US 11,700,129 B2
(45) Date of Patent: Jul. 11, 2023

(54) SYSTEMS AND METHODS FOR TOKENIZED DATA DELEGATION AND PROTECTION

(71) Applicant: Capital One Services, LLC, McLean, VA (US)

(72) Inventors: Qiaochu Tang, The Colony, TX (US); Jason Hoover, Grapevine, TX (US); Micah Price, Plano, TX (US); Stephen Wylie, Carrollton, TX (US); Geoffrey Dagley, McKinney, TX (US)

(73) Assignee: CAPITAL ONE SERVICES, LLC, McLean, VA (US)

( * ) Notice: Subject to any disclaimer, the term of this patent is extended or adjusted under 35 U.S.C. 154(b) by 358 days.

(21) Appl. No.: 16/906,705

(22) Filed: Jun. 19, 2020

(65) Prior Publication Data

US 2021/0144010 A1 May 13, 2021

Related U.S. Application Data

(63) Continuation of application No. 16/683,133, filed on Nov. 13, 2019, now Pat. No. 10,735,198.

(51) Int. Cl.
*H04L 9/32* (2006.01)
*H04L 9/40* (2022.01)
*G06N 20/00* (2019.01)

(52) U.S. Cl.
CPC .......... *H04L 9/3234* (2013.01); *G06N 20/00* (2019.01); *H04L 63/06* (2013.01); *H04L 63/083* (2013.01); *H04L 63/102* (2013.01)

(58) Field of Classification Search
CPC ..... H04L 9/3234; H04L 63/06; H04L 63/083; H04L 63/102; H04L 9/3215; H04L 9/3213; G06N 20/00
See application file for complete search history.

(56) References Cited

U.S. PATENT DOCUMENTS

| | | | |
|---|---|---|---|
| 6,438,690 B1 | 8/2002 | Patel et al. |
| 7,187,772 B2 | 3/2007 | Vora et al. |
| 7,958,540 B2 | 6/2011 | Saxena |
| 8,032,743 B2 | 10/2011 | Asay et al. |
| 8,473,735 B1 | 6/2013 | Jarvie et al. |

(Continued)

OTHER PUBLICATIONS

White Paper "Detecting and Preventing Banking Application Fraud", SAS Institute Inc, SAS.com/Fraud, 109917 (8 pages).

(Continued)

*Primary Examiner* — Mohammad W Reza
(74) *Attorney, Agent, or Firm* — Hunton Andrews Kurth LLP

(57) ABSTRACT

Example embodiments of systems and methods for data delegation and control through the use of tokenized data are provided. In an exemplary method of data delegation and control, a data device may store private information associated with a user and generate an access token, comprising tokenized data identifying the data device. The data device may transmit the access token to a user device through a front channel and receive an information request from a merchant device comprising the access token through a secure back channel. Upon authenticating the access token, the data device may transmit a portion of the private information to the merchant device through the secure back channel.

20 Claims, 6 Drawing Sheets

(56) References Cited

U.S. PATENT DOCUMENTS

| | | |
|---|---|---|
| 8,572,391 B2 | 10/2013 | Golan et al. |
| 8,935,524 B1 | 1/2015 | Lawrence |
| 2001/0020228 A1 | 9/2001 | Cantu et al. |
| 2002/0007346 A1 | 1/2002 | Qiu et al. |
| 2002/0035686 A1 | 3/2002 | Creighton et al. |
| 2002/0038291 A1 | 3/2002 | Petersen et al. |
| 2003/0110401 A1 | 6/2003 | Aoshima et al. |
| 2003/0163694 A1 | 8/2003 | Chen et al. |
| 2004/0093502 A1 | 5/2004 | Shurygailo et al. |
| 2005/0021975 A1 | 1/2005 | Liu |
| 2005/0160298 A1 | 7/2005 | Reno |
| 2006/0020783 A1 | 1/2006 | Fisher |
| 2006/0123227 A1 | 6/2006 | Miller et al. |
| 2008/0082354 A1 | 4/2008 | Hurry et al. |
| 2008/0209209 A1 | 8/2008 | Gupta et al. |
| 2011/0197061 A1 | 8/2011 | Chou et al. |
| 2011/0296522 A1 | 12/2011 | Speyer et al. |
| 2014/0074637 A1 | 3/2014 | Hammad |
| 2014/0149738 A1 | 5/2014 | Rhelimi |
| 2017/0099146 A1* | 4/2017 | Sharma .................. H04L 63/168 |
| 2017/0109736 A1 | 4/2017 | Heiman et al. |
| 2017/0186001 A1* | 6/2017 | Reed ...................... H04L 9/3226 |
| 2017/0346639 A1 | 11/2017 | Muftic |
| 2018/0041488 A1 | 2/2018 | Kohli |
| 2018/0322270 A1* | 11/2018 | Bailey ................... H04L 63/083 |
| 2019/0020474 A1* | 1/2019 | Kurian .................... G06F 21/64 |

OTHER PUBLICATIONS

The Client ID and Secret, OAuth 2.0, downloaded from the Internet: https://www.oauth.com/oauth2-servers/client-registration/client-id-secret/.

* cited by examiner

SYSTEMS AND METHODS FOR TOKENIZED DATA DELEGATION AND PROTECTION

CROSS REFERENCE TO RELATED APPLICATION

The subject application is a continuation of U.S. patent application Ser. No. 16/683,133 filed Nov. 13, 2019, the contents of which is hereby incorporated by reference in its entirety.

FIELD OF THE INVENTION

The present disclosure relates to the data access and control, and more particularly, to systems and methods for data delegation and protection using tokenized data.

BACKGROUND

Every individual has a large amount of personal data, and this data may often include private, sensitive information, such as account numbers, a birth date, and a Social Security number. This private information may often be used to for identification or transaction purpose, and therefore identity thieves, hackers, fraudsters, and other criminals may try gain unauthorized access to an individual's private information. If an individual's private information is compromised, identity theft, fraud, and other illegal activities may occur, which may damage the individual's finances, access to credit, and reputation. Significant expenditures of money, time, and other resources may be required to make an individual whole, or at least somewhat whole, after private information has been comprised.

Many entities do business with the private, sensitive information of individuals, including without limitation financial institutions, government agencies, and many other commercial and industrial entities. Accordingly, entities place a premium on data security, and face substantial liability if private information is exposed. The needs for data security can discourage or hinder transactions, including by requiring customers or potential customers to provide private information as part of the purchases process. In addition, data security needs can increase costs and divert resources from other uses.

The risk that private information may be compromised may increase with the frequency with which it is used. The more an individual, or an entity on the individual's behalf, engages in transactions that expose or involve private information, the more likely the private information is compromised. In particular, electronic transactions often require the use of private information, and as electronic transactions become an increasingly large share of commercial activity, data security risks also increase. In addition, personal computing devices, such as smartphones, laptops, and tablets, are often used to conduct electronic transactions. Since such devices may rely on wireless data connections and are portable, the risk that some private information is intercepted or stolen may increase.

These and other deficiencies exist. Accordingly, there is a need to provide individuals and entities with an appropriate solution that overcomes these deficiencies to provide data security for private information while facilitating transactions and other activities involving such information.

SUMMARY

Aspects of the disclosed technology include systems and methods for data access and control through the delegation and protection of tokenized data. Various embodiments describe systems and methods for implementing and managing the delegation and protection of tokenized data, which may include private, sensitive information.

Embodiments of the present disclosure provide a method of data delegation and control, comprising: storing, by a data device, private information associated with a user; generating, by the data device, an access token, wherein the access token comprises tokenized data identifying the data device; transmitting, by the data device through a first front channel, the access token to a user device; receiving, by the data device through a first secure back channel, an information request comprising the access token, from a merchant device; authenticating, by the data device, the access token; and transmitting, by the data device through the first secure back channel, a portion of the private information, to the merchant device.

Embodiments of the present disclosure provide a system for data delegation and control, comprising: a user device comprising a processor and a memory; a data device comprising a processor and a memory, wherein the data device is in data communication with a database containing private information; and a requesting device comprising a processor and a memory, wherein, upon receipt of a request for an access token from the user device, the data device is configured to generate an access token associated with the private information, and transmit the access token to the user device via a front channel, and wherein, upon receipt of an information request from the requesting device through a secure back channel, the information request comprising the access token, a secret key, and an identification of a portion of private information, the data device is configured to: authenticate the access token and the secret key; retrieve the portion of private information; and transmit the portion of private information to the requesting device through the secure back channel.

Embodiments of the present disclosure provide a non-transitory computer-accessible medium having stored thereon computer-executable instructions for providing data delegation and control, wherein, when a computer arrangement executes the instructions, the computer arrangement comprising a processor in data communication with a database containing private information, wherein the computer arrangement is configured to perform procedures comprising: receiving, through a front channel, a request for an access token associated with the private information; generating an access token, the access token comprising a tokenized identifier for the computer arrangement; transmitting the access token through the front channel; receiving, through a secure back channel, the access token, a secret key, and a request for a first portion of private information; authenticating the access token and secret key; requesting, through the secure back channel, a second portion of private information; receiving, through the secure back channel, a third portion of private information; comparing the third portion of private information to the private information contained in the database; generating a similarity score based on the comparison; and transmitting the first portion of private information through the secure back channel if the similarity score exceeds a threshold.

Further features of the disclosed design, and the advantages offered thereby, are explained in greater detail hereinafter with reference to specific example embodiments illustrated in the accompanying drawings.

DETAILED DESCRIPTION OF EXAMPLE EMBODIMENTS

The following description of embodiments provides non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention.

Example embodiments of the present disclosure provide systems and methods for data access and control that promote data security by reducing the frequency and methods by which sensitive private information can be sent. As used herein, private information can include any sensitive data, including financial data (e.g., account information, account numbers, account balances, account activity), personal information (e.g., Social Security number, home or work address, birth date, telephone number, email address, passport number, driver's license number), access information (e.g., passwords, security codes, authorization codes, biometric data), and any other information that user may desire to avoid revealing to unauthorized persons. By restricting the transmission of private information to certain instances and through the use of tokenized data, example embodiments of the present disclosure may reduce the risk that private information is compromised when it is being sent, stored, or viewed. In addition, by reducing the occurrences when private information is sent, the odds of any unauthorized data exposure may be reduced.

Further, many entities that handle sensitive private information or conduct transactions involving sensitive private information may benefit from effectively and efficiently verifying identities while reducing the risk of exposure that information. These benefits may include more effective and efficient compliance with "Know Your Customer" (KYC) regulations, improving the likelihood that identities, information, and transactions can be trusted. For example, financial institutions, insurers, and other entities may expend significant resources complying with KYC regulations and other fraud prevention tasks, and these resource expenditures may be reduced through the improved systems and methods of data security and customer and transaction verification described herein.

Figure 1:
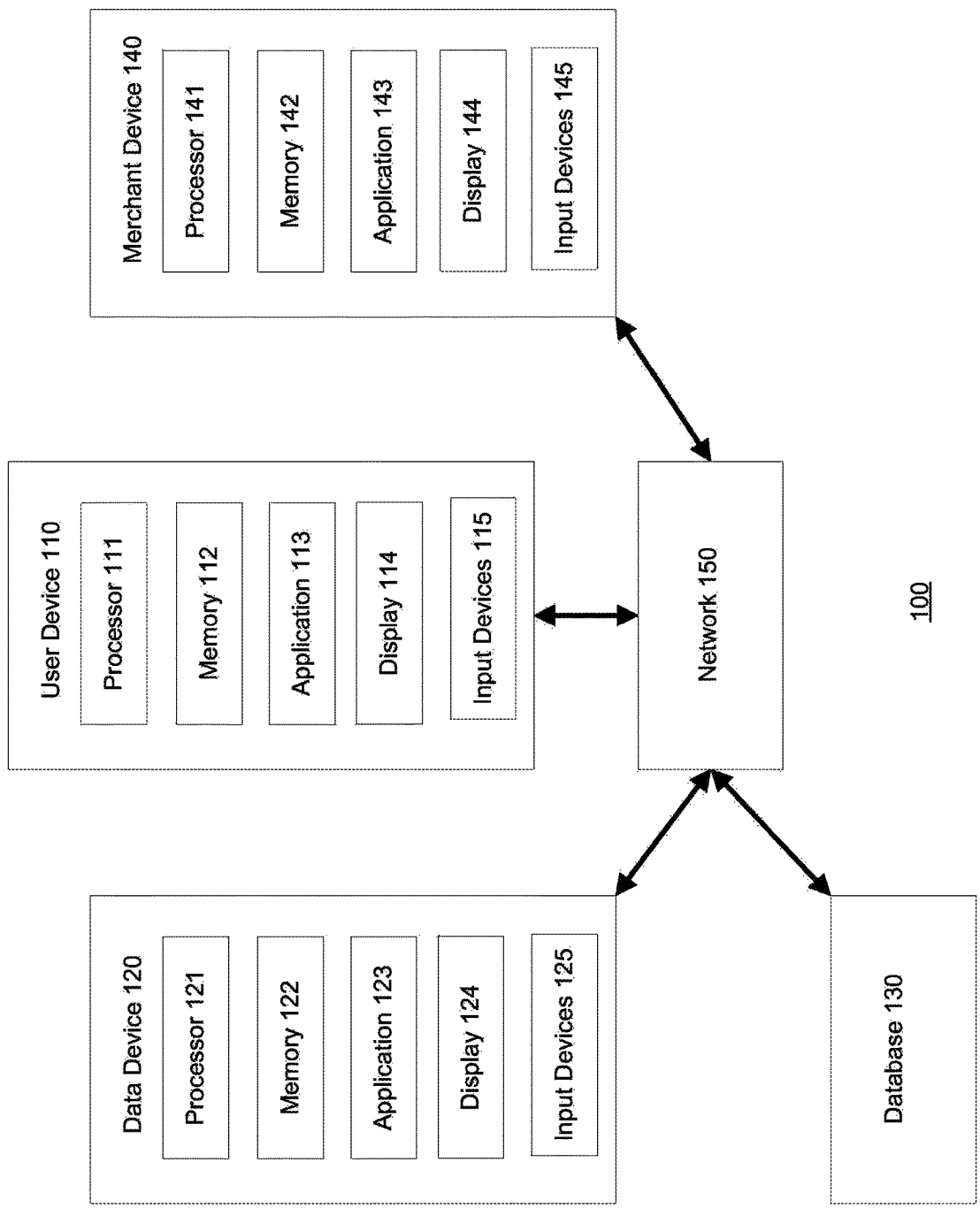
FIG. 1 is a diagram of a data delegation and control system according to an example embodiment.

FIG. 1 illustrates a data delegation and control system according to an example embodiment. As further discussed below, system 100 may include a user device 110, a data device 120, a database 130, and a merchant device 140 in communication via a network 165. Although FIG. 1 illustrates single instances of the components, system 100 may include any number of components.

The user device 110 may be a network-enabled computer device. Exemplary network-enabled computer devices include, without limitation, including, a server, a network appliance, a personal computer, a workstation, a phone, a handheld personal computer, a personal digital assistant, a thin client, a fat client, an Internet browser, a mobile device, a kiosk, or other a computer device or communications device. For example, network-enabled computer devices may include an iPhone, iPod, iPad from Apple® or any other mobile device running Apple's iOS® operating system, any device running Microsoft's Windows® Mobile operating system, any device running Google's Android® operating system, and/or any other smartphone, tablet, or like wearable mobile device.

The user device 110 may include a processor 111, a memory 112, an application 113, a display 114 and input devices 115. The processor 111 may be a processor, a microprocessor, or other processor, and the user device 105 may include one or more of these processors. The processor 111 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 111 may be coupled to the memory 112. The memory 112 may be a read-only memory, write-once read-multiple memory or read/write memory, e.g., RAM, ROM, and EEPROM, and user deice may include one or more of these memories. A read-only memory may be factory programmable as read-only or one-time programmable. One-time programmability provides the opportunity to write once then read many times. A write once/read-multiple memory may be programmed at a point in time after the memory chip has left the factory. Once the memory is programmed, it may not be rewritten, but it may be read many times. A read/write memory may be programmed and re-programed many times after leaving the factory. It may also be read many times. The memory 112 may be configured to store one or more software applications, such as application 113, and other data, such as private information.

The application 113 may comprise one or more software applications comprising instructions for execution on the user device 105. In some examples, user device 110 may execute one or more applications, such as software applications, that enable, for example, network communications with one or more components of system 100, transmit and/or receive data, and perform the functions described herein. Upon execution by the processor 111, the application 113 may provide the functions described in this specification, specifically to execute and perform the steps and functions in the process flows described above. Such processes may be implemented in software, such as software modules, for execution by computers or other machines. The application 113 may provide graphic user interfaces (GUIs) through which user may view and interact with other components and devices within system 100. The GUIs may be formatted, for example, as web pages in HyperText Markup Language (HTML), Extensible Markup Language (XML) or in any other suitable form for presentation on a display device depending upon applications used by users to interact with the system 100.

The user device 110 may further include a display 114 and input devices 115. The display 114 may be any type of device for presenting visual information such as a computer monitor, a flat panel display, and a mobile device screen, including liquid crystal displays, light-emitting diode displays, plasma panels, and cathode ray tube displays. The input devices 115 may include any device for entering information into the user device 110 that is available and supported by the user device 110, such as a touch-screen, keyboard, mouse, cursor-control device, touch-screen, microphone, digital camera, video recorder or camcorder. These devices may be used to enter information and interact with the software and other devices described herein.

The data device 120 may be a network-enabled computer device. Exemplary network-enabled computer devices include, without limitation, a server, a network appliance, a personal computer, a workstation, a phone, a handheld personal computer, a personal digital assistant, a thin client, a fat client, an Internet browser, a mobile device, a kiosk, or other a computer device or communications device. For example, network-enabled computer devices may include an iPhone, iPod, iPad from Apple® or any other mobile device running Apple's iOS® operating system, any device running Microsoft's Windows® Mobile operating system, any device running Google's Android® operating system, and/or any other smartphone, tablet, or like wearable mobile device.

The data device 120 may include a processor 121, a memory 122, and an application 123. The processor 121 may be a processor, a microprocessor, or other processor, and the data device 135 may include one or more of these processors. The processor 121 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 121 may be coupled to the memory 122. The memory 122 may be a read-only memory, write-once read-multiple memory or read/write memory, e.g., RAM, ROM, and EEPROM, and user deice may include one or more of these memories. A read-only memory may be factory programmable as read-only or one-time programmable. One-time programmability provides the opportunity to write once then read many times. A write once/read-multiple memory may be programmed at a point in time after the memory chip has left the factory. Once the memory is programmed, it may not be rewritten, but it may be read many times. A read/write memory may be programmed and re-programed many times after leaving the factory. It may also be read many times. The memory 122 may be configured to store one or more software applications, such as application 122, and other data, such as private information.

The application 123 may comprise one or more software applications comprising instructions for execution on the data device 123. In some examples, data device 120 may execute one or more applications, such as software applications, that enable, for example, network communications with one or more components of system 100, transmit and/or receive data, and perform the functions described herein. Upon execution by the processor 121, the application 123 may provide the functions described in this specification, specifically to execute and perform the steps and functions in the process flows described above. Such processes may be implemented in software, such as software modules, for execution by computers or other machines. The application 123 may provide graphic user interfaces (GUIs) through which user may view and interact with other components and devices within system 100. The GUIs may be formatted, for example, as web pages in HyperText Markup Language (HTML), Extensible Markup Language (XML) or in any other suitable form for presentation on a display device depending upon applications used by users to interact with the system 100.

The data device 120 may further include a display 124 and input devices 125. The display 124 may be any type of device for presenting visual information such as a computer monitor, a flat panel display, and a mobile device screen, including liquid crystal displays, light-emitting diode displays, plasma panels, and cathode ray tube displays. The input devices 125 may include any device for entering information into the data device 120 that is available and supported by the data device 120, such as a touch-screen, keyboard, mouse, cursor-control device, touch-screen, microphone, digital camera, video recorder or camcorder. These devices may be used to enter information and interact with the software and other devices described herein.

The database 130 may be one or more databases configured to store date, including without limitation, private information. The database 130 may comprise a relational database, a non-relational database, or other database implementations, and any combination thereof, including a plurality of relational databases and non-relational databases. In some examples, the database 130 may comprise a desktop database, a mobile database, or an in-memory database. Further, the database 130 may be hosted internally by the data device 120 or may be hosted externally of the data device 120, such as by a server, by a cloud-based platform, or in any storage device that is in data communication with the data device 120.

The merchant device 140 may be a network-enabled computer device. Exemplary network-enabled computer devices include, without limitation, including, a server, a network appliance, a personal computer, a workstation, a phone, a handheld personal computer, a personal digital assistant, a thin client, a fat client, an Internet browser, a mobile device, a kiosk, or other a computer device or communications device. For example, network-enabled computer devices may include an iPhone, iPod, iPad from Apple® or any other mobile device running Apple's iOS® operating system, any device running Microsoft's Windows® Mobile operating system, any device running Google's Android® operating system, and/or any other smartphone, tablet, or like wearable mobile device.

The merchant device 140 may include a processor 141, a memory 142, and an application 143. The processor 141 may be a processor, a microprocessor, or other processor, and the merchant device 140 may include one or more of these processors. The processor 141 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 141 may be coupled to the memory 142. The memory 142 may be a read-only memory, write-once read-multiple memory or read/write memory, e.g., RAM, ROM, and EEPROM, and user deice may include one or more of these memories. A read-only memory may be factory programmable as read-only or one-time programmable. One-time programmability provides the opportunity to write once then read many times. A write once/read-multiple memory may be programmed at a point in time after the memory chip has left the factory. Once the memory is programmed, it may not be rewritten, but it may be read many times. A read/write memory may be programmed and re-programed many times after leaving the factory. It may also be read many times. The memory 142 may be configured to store one or more software applications, such as application 143, and other data, such as private information.

The application 143 may comprise one or more software applications comprising instructions for execution on the merchant device 140. In some examples, merchant device 140 may execute one or more applications, such as software applications, that enable, for example, network communications with one or more components of system 100, transmit and/or receive data, and perform the functions described herein. Upon execution by the processor 141, the application 143 may provide the functions described in this specification, specifically to execute and perform the steps and functions in the process flows described above. Such processes may be implemented in software, such as software modules, for execution by computers or other machines. The application 143 may provide graphic user interfaces (GUIs) through which user may view and interact with other components and devices within system 100. The GUIs may be formatted, for example, as web pages in HyperText Markup Language (HTML), Extensible Markup Language (XML) or in any other suitable form for presentation on a display device depending upon applications used by users to interact with the system 100.

The merchant device 140 may further include a display 144 and input devices 145. The display 144 may be any type of device for presenting visual information such as a computer monitor, a flat panel display, and a mobile device screen, including liquid crystal displays, light-emitting diode displays, plasma panels, and cathode ray tube displays. The input devices 145 may include any device for entering information into the merchant device 140 that is available and supported by the merchant device 140, such as a touch-screen, keyboard, mouse, cursor-control device, touch-screen, microphone, digital camera, video recorder or camcorder. These devices may be used to enter information and interact with the software and other devices described herein.

System 100 may include one or more networks 150. In some examples, network 150 may be one or more of a wireless network, a wired network or any combination of wireless network and wired network, and may be configured to connect user device 110 to data device 120, user device 110 to merchant device 140, data device 120 to database 130, and data device 110 to merchant device 140. For example, network 150 may include one or more of a fiber optics network, a passive optical network, a cable network, an Internet network, a satellite network, a wireless local area network (LAN), a Global System for Mobile Communication, a Personal Communication Service, a Personal Area Network, Wireless Application Protocol, Multimedia Messaging Service, Enhanced Messaging Service, Short Message Service, Time Division Multiplexing based systems, Code Division Multiple Access based systems, D-AMPS, Wi-Fi, Fixed Wireless Data, IEEE 802.11b, 802.15.1, 802.11n and 802.11g, Bluetooth, NFC, Radio Frequency Identification (RFID), Wi-Fi, and/or the like.

In addition, network 150 may include, without limitation, telephone lines, fiber optics, IEEE Ethernet 902.3, a wide area network, a wireless personal area network, a LAN, or a global network such as the Internet. In addition, network 150 may support an Internet network, a wireless communication network, a cellular network, or the like, or any combination thereof. Network 150 may further include one network, or any number of the exemplary types of networks mentioned above, operating as a stand-alone network or in cooperation with each other. Network 150 may utilize one or more protocols of one or more network elements to which they are communicatively coupled. Network 150 may translate to or from other protocols to one or more protocols of network devices. Although network 150 is depicted as a single network, it should be appreciated that according to one or more examples, network 150 may comprise a plurality of interconnected networks, such as, for example, the Internet, a service provider's network, a cable television network, corporate networks, such as credit card association networks, and home networks. Network 150 may further comprise, or be configured to create, one or more front channels, which may be publicly accessible and through which communications may be observable, and one or more secured back channels, which may not be publicly accessible and through which communications may not be observable.

In some examples, communications between the user device 110, data device 120, and merchant device 140 via network 150 can occur via one or more front channels and one or more secure back channels. A front channel may be a communication protocol that employs a publicly accessible and/or unsecured communication channel such that a communication sent to user device 110, data device 120, and/or merchant device 140 may originate from any other device, whether known or unknown to user device 110, data device 120, and/or merchant device 140, if that device possesses the address (e.g., network address, Internet Protocol (IP) address) of the user device 110, data device 120, and/or merchant device 140. Exemplary front channels include, without limitation, the Internet, an open network, and other publicly-accessible communication networks. In some examples, communications sent via a front channel may be subject to unauthorized observation by another device. In some examples, front channel communications may comprise Hypertext Transfer Protocol (HTTP) secure socket layer (SSL) communications, HTTP Secure (HTTPS) communications, and browser-based communications with a server or other device.

A secure back channel may be a communication protocol that employs a secured and/or publicly inaccessible communication channel. A secure back channel communication sent to user device 110, data device 120, and/or merchant device 140 may not originate from any device, and instead may only originate from a selective number of parties. In some examples, the selective number of devices may comprise known, trusted, or otherwise previously authorized devices. Exemplary secure back channels include, without limitation, a closed network, a private network, a virtual private network, an offline private network, and other private communication networks. In some examples, communications sent via a secure back channel may not be subject to unauthorized observation by another device. In some examples, secure back channel communications may comprise Hypertext Transfer Protocol (HTTP) secure socket layer (SSL) communications, HTTP Secure (HTTPS) communications, and browser-based communications with a server or other device.

In some examples, user device 110 can be associated with a user and may be operated by that user. The data device 120 can be associated with data holding entity, such as a commercial institution (e.g., a financial institution or an employer), a government agency, or other entity, and may be operated by the entity. The user device 110 may transmit, via a secure back channel, private information for storage within the memory 122 of the data device 120 or within the database 130. In other examples, the user may provide private information to entity operating the data device in an offline manner, such as through the submission of a paper form or a telephone call. One received, the private information may be securely stored in the memory 122 of the data device 120 or within the database 130. Security measures, including encryption, multifactor authentication, biometric authentication, and other measures can be implemented to increase the security of the private information and reduce the likelihood that the private information can be compromised while being stored.

If requested by the user (via the user device 105 or via an offline method), the data device 120 may generate an access token. The access token may be associated with the user and/or with the user's stored private information or with a subset of the user's stored private information. In some examples, the access token may be a random number. In other examples, the access token may be a tokenized version of the user's name, account number, user identifier, a portion of the private information, or a combination thereof. In other examples, the access token may be created without reference to the user or the private information, and instead may be generated with reference to the data holding entity (e.g., based on an identifier for the data holding entity or a sequence number) or may be randomly generated. For example, the access token may comprise tokenized data identifying the data device and/or the data holding entity. Since the access token has been created in this manner, it does not contain any private information relating to the user. As an example, the access token may be a JavaScript Object Notation (JSON) web token.

The access token may be selectively configured by the user to allow access to all of the user's stored private information or one or more portions thereof. For example, a user may specify that an access token allow access to all private information stored by a particular data holding entity. As another example, a user may specify that only a particular item of private information (e.g., an account number, a mailing address, a Social Security number, salary information, a password, a security code) is accessible, and accordingly the access token may be configured to grant only that access and may be uniquely associated with the specified information.

As another example, the user may specify that an access token grant access to a specific category of information, such as contact information (e.g., home address, mailing address, telephone number, email address), identity information (e.g., legal name, residence address, Social Security number), financial information (e.g., account number(s), account balance, account history, credit history, trade or transaction approval information), and security information (e.g., a password, a security code, a biometric identifier, second factor authentication information). In some examples, the categories may be transaction-based and comprise the private information necessary to complete a certain transaction. For example, a user seeking to complete a transfer of funds between financial accounts could authorize access to account numbers, account balances, passwords, and security codes. In another example, a user seeking to transfer medical records between health care providers could authorize access to patient identifiers, provider identifiers, passwords, security codes, and medical records. The medical record access could be to all medical records related to the patient at one or more providers, all medical records from a certain time period, all medical records pertaining to a certain diagnosis, medical issue, or medical area (e.g., cardiovascular health, mental health).

As another example, the user may specify that an access token grant access to certain data to certain entities. For example, a user may specify that financial institutions may receive access to account numbers, account balances, account histories, passwords, security codes, and to a Social Security numbers. As another example, the user may specify that medical providers may have access to patient identifiers, providers identifiers, passwords, security codes, and medical records.

Upon creation, the access token may be provided to the user, e.g., for storage within the memory 112 of the user device 110. Since the access token does not contain or reveal any private information, the access token may be transmitted from the data device 120 to the user device 110 via an unsecured front channel. In other examples, the access token may be transmitted from the data device 120 to the user device 110 via a secure back channel, which may provide an additional security benefit of not allowing an unauthorized observer to the transmission to associate the access token with both the user device 110 and the data device 120 (and potentially by extension, with the user and the data holding entity).

The user may present the access token to a merchant in lieu of providing private information when engaging in a transaction or other activity requiring the exchange of private information. Since the access token does not contain or reveal any private information, the transmission of the access token from user device 110 to merchant device 140 may occur via an unsecured front channel. In other examples, the access token may be transmitted from the data device 120 to the user device 110 via a secure back channel, which may provide an additional security benefit of not allowing an unauthorized observer to the transmission to associate the access token with both the user device 110 and the merchant device 140 (and potentially by extension, with the user and the data holding entity).

In some examples, the user may present the access token to the merchant device 140 via a browser extension operable on the user device 110. When loading and/or viewing a webpage, the browser extension may recognize one or more webpage elements as requesting certain private information. In response, the browser extension may request the creation of an access token based on the private information request and the user's settings and preferences. The browser extension may also be configured to prompt the user for review, configuration, and approval of the grant of access to the private information and the creation of the token as needed. Once the access token has been generated, the browser extension may transmit the access token to the merchant device 140.

In some examples, the user may request the creation of an access token via the user device 110. For example, a message, prompt, push notification, email, text, telephone call or other notification requesting certain private information may be received by the user device 110 to alert the user that certain private information has been requested. The user may request the access token be created by, e.g., a front-end request field provided by the data-holding entity. The user may directed to the field by, e.g., directions or a link received in the notification, and may identify or select the information to be provided (which may include some or all of the requested private information and/or other information) and the conditions or restrictions on this information. The user may also be required to input a password, security code, or other security measure, which may be received in the notification or separately, as a form of multi-factor authentication.

In other examples, the functionality described above with respect to the browser extension or the user interaction may be implemented in one or more separate applications. The separate applications may be proprietary applications for one or more of the data holding entities. As another example, the separate applications may be one or more third party applications configured to communicate with the data-holding entities.

Upon receipt of the access token, the merchant device 140 may store the access token in memory 142 and may further transmit the access token to data device 120. By transmitting the access token to the data device 120, the merchant device 140 may be requesting the private information associated with the access token from the data device 120. As before, the access token may be transmitted from the merchant device 140 to the data device 120 via an unsecure front channel or via a secure back channel. In some examples, the transmission of the access token may be accompanied by a request for specific private information. In these examples, the access token and request may be transmitted via a secure back channel.

Upon receipt of the data access token, the data device 120 may authenticate the token to confirm the token's validity and determine what private information is associated with the access token. The data device 120 may collect the private information associated with the access token or, if specific private information has been requested by the merchant device 140, that specific private information, or a combination thereof, from the memory 122 and/or the database 130. The data device 120 may then transmit the collected private information to the merchant device 140 through a secure back channel.

In some examples, the merchant device 140 may possess or generate a secret key that is to be transmitted to the data device 120 along with the access token and private information request. This secret key can be authenticated by the data device 120 in order to verify the identity of the merchant device 140 (and/or the merchant associated with the merchant device 140) prior to transmitting any private information in response to the access token or private information request. In some examples, the secret key can be generated using symmetric encryption, a public/private key pair, message authentication code, or other cryptographic method. In other examples, the secret key may be assigned to and stored by the merchant device, instead of being generated. As an example, the secret key may comprise an OAuth client secret. The use of a secret key along with the access token may further increase security and reduce the likelihood that the private information may be compromised.

In some examples, prior to the transmission of any private information from the data device 120 to the merchant device 140, the data device 120 may send a notification and/or a message to the user device 110 that private information associated with the user has been requested. In some examples, the data device 120 may wait to transmit the private information to the merchant device 140 until confirmation that the transmission is approved is received from the user device 110 (e.g., a message from the user device 110 approving the transmission). If approval is received, the private information may be transmitted. If approval is not received or if approval is denied, the private information may not be transmitted. Alternatively, if the merchant device 140 is recognized as a trusted or verified merchant, the data transmission may proceed unless disapproval of the transmission is received within a predetermined time period.

In some examples, the data device 120 may generate a temporary access token. The temporary access token may be a one-time use access token, a token limited to a certain number of uses, and/or a token limited to a specified time period. In other examples, the access token may be permanent, such that it may be used an indefinite number of times. A permanent access token may be cancelled by the user device 110, the data device 120, or the merchant device 140.

The type of access token created may be based on the user request. As another example, the type of access token may be determined by the data device 120, based on, e.g., a data security policy, the merchant device 140 requesting access to the private information, the frequency with which the private information has been, or is expected to be, accessed, the merchant associated with the merchant device 140, In some examples, the type of access token created may be based on the merchant device 140 that is requesting private information. For example, if the merchant device 140 has previously requested private information successfully, a temporary access token having a longer duration and/or greater number of uses, or a permanent access token, may be created. As other examples, if the merchant device 140 or the merchant associated with the merchant device 140 has been previously authorized, identified as trustworthy, and/or is a member of a trusted network, then a temporary access token having a longer duration and/or greater number of uses, or a permanent access token, may be created. However, if the merchant device 140 has not successfully requested private information before, or if the merchant device 140 or the merchant associated with the merchant device 140 has not been previously authorized, not identified as trustworthy, and/or is not a member of a trusted network, then a temporary access token having a shorter duration and/or lower number of uses may be created.

Accordingly, by reducing the number of times the private information is transmitted via unsecured front channels, and replacing those transmissions with access tokens that do not reveal any private information, the risk of the private information being compromised as a transaction is taking place may be reduced. By increasing the transmissions of private information over secured back channels, the risk of compromise may be further reduced.

In addition, by providing access tokens of varying durations and uses data security may be improved and the risk of misuse of access tokens may be reduced. Further, through the use of verifiable access tokens and in some cases secret keys, the ability of identity thieves or other fraudsters to gain unauthorized access to private information may be reduced.

Example embodiments provide an additional data security benefit by increasingly limiting private date storage to the data device 120, which may employ stronger data security equipment and practices than implemented on the merchant device 140. Thus, the user's private information, in a significant amount or in its entirety, may most frequently be stored in a highly secure environment.

In some examples, only merchants meeting certain security requirements can be permitted to use the access tokens and/or secret keys. For example, only merchants with sufficiently secure data storage and with sufficiently secure back channels can be allowed to receive and send access tokens. In some examples, only merchants meeting even higher security requirements can be permitted to receive or generate secret keys. In some examples, the duration and number of uses of access tokens can be adjusted based on the security capabilities of each merchant. Thus, the requirements described by the present disclosure may incentivize data security improvements by one or more merchants, which may benefit the merchants, the data holding entities, and users.

Figure 2:
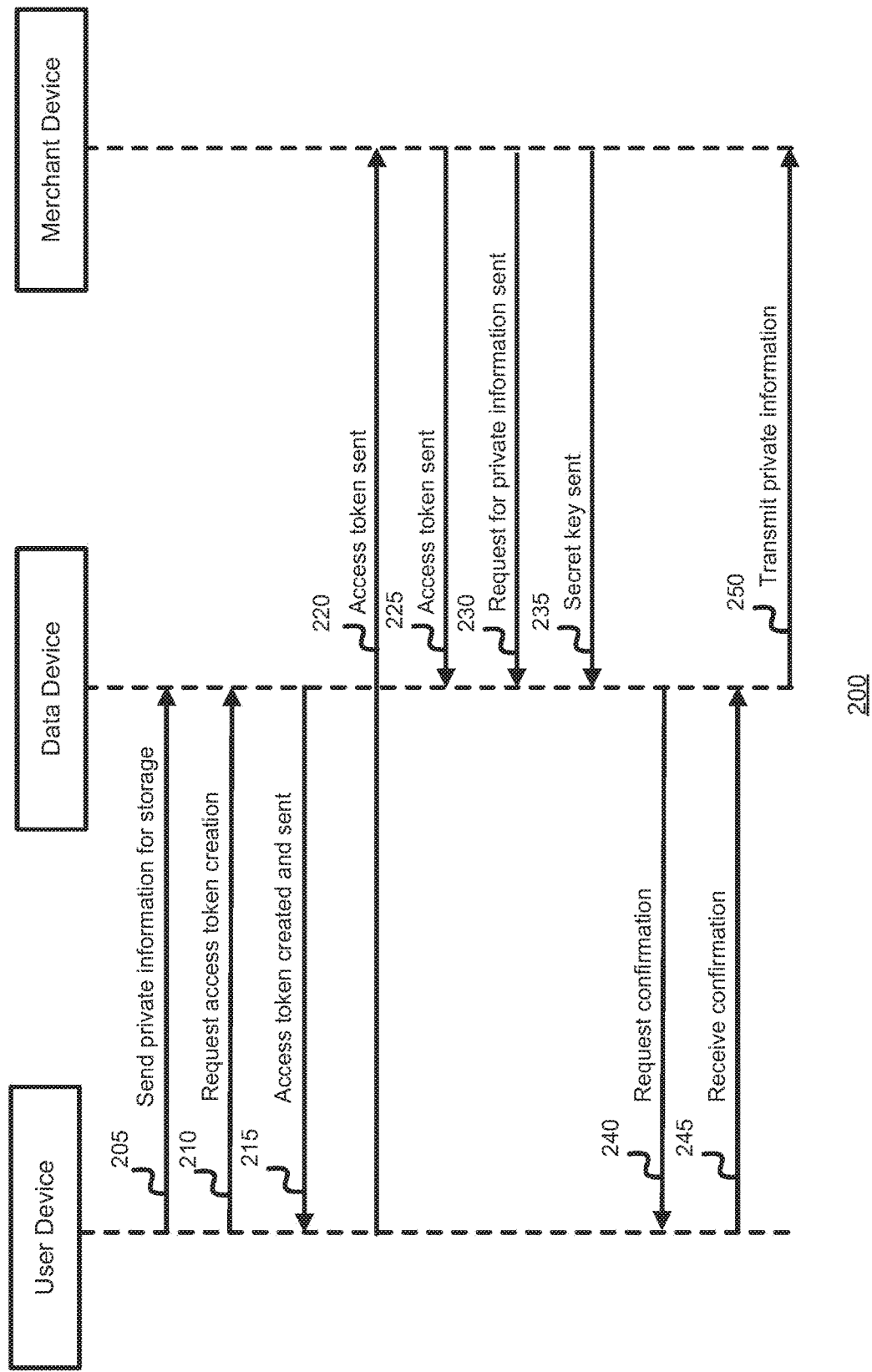
FIG. 2 is a sequence diagram for data delegation and control according to an example embodiment.

FIG. 2 illustrates a sequence diagram for data delegation and control according to an example embodiment. FIG. 2 may reference the same or similar components as those illustrated in FIG. 1, including a user device, a data device, a database, and a merchant device.

The method 200 may commence at step 205, where a user sends private information via a user device to a data device operated by a data holding entity for storage. The data holding entity may store the private information within an internal database and/or within an external database. In either case, the data holding entity may apply a high level of security when storing the private information.

In some examples, the data device may collect information relating to the user, information relating to the user's activities, or information from other sources. For example, the data device may collect information based on a user's interaction with one or more accounts. As another example, the data device may collect information based on the user's interaction one or more applications, including third party applications. As another example, it is understood that the data device may obtain data from third party data sources. Accordingly, it is understood that data stored by the data device need not be directly provided by the user.

In some examples, prior to the acceptance of private information at step 205, the data device may perform a verification procedure to confirm the user's identity. The verification procedure may include, without limitation, requesting a login credential (e.g., a user name, a password, a security code, a biometric identifier) via the user device, requiring the establishment of an account for the user, and requiring the completion of a multifactor authentication.

In step 210, the user may request an access token be created by the data holding entity. The access token may be associated with the user and/or the private information or a subset thereof, and may allow the user to provide the token to a merchant in lieu of private information. The access token may be a tokenized version of information relating to the user, the user's account, the private information, or without any association thereto. Instead, the access token may be generated with reference to an identifier created by the data holding entity. In other examples, the access token may be created randomly. Once created, the access token can be sent to the user device and available for use by the user. Since the access token does not include any private information, the access token may be sent to the user device by the data device through an unsecured front channel.

In step 220, the user may send the access token from the user device to a merchant device as part of a transaction. The access token may be sent in place of private information, with the intention that the merchant can use the access token to obtain private information for the transaction from the data holding entity. Since the access token does not include any private information, the user device may send the access token to the merchant device via an unsecured front channel.

Upon receipt of the access token in step 225, the merchant device may recognize that the access token is associated with the data holding entity. In some examples, this recognition may occur because the access token includes an identifier associated with the data holding entity and/or the data device. In other examples, the merchant device may recognize that any tokens received having a certain format are associated with the data holding entity and/or data device. Once this recognition is made, the merchant device may establish a secure back channel for communication with the data device, and may send the access token to the data device via this channel.

In some examples, in step 230, the merchant device may also send a request for private information to the data device via the secure back channel. The request may identify the particular private information required for the transaction, so only the private information necessary for the transaction is sent to the merchant device. In other examples, the access token itself, once authenticated, may identify the private information necessary for the transaction.

In some examples, it may be determine whether the user device, data device, and/or merchant device (or other device within the system) are trusted device and/or operated by trusted parties. This determination may be made in advance of, or during, the processing of a transaction. For example, only previously-verified or pre-authorized devices may utilize the access token and related functionality. These devices may include devices that have been authorized or verified individually or as part of an authorized or verified network. In other examples, upon receiving a request for private information, a device may be verified or authorized prior to proceeding. In some examples, the verification or authorization applicable to a given device may define or limit the type or amount of data that each device may receive. For example, no access tokens intended for devices associated with financial institutions may grant access to private information relating to a user's health or medical records. As another example, no access token intended for devices associated a medical institution may access private information relating to a user's educational information or academic records. However, it is understood that these configurations could be overridden if necessary for a particular transaction (e.g., a medical institution interviewing a user for potential employment may need to obtain private information relating to the user's educational records).

In some examples, in step 235, a secret key may be sent from the merchant device to the data device. The use of a secret key may provide additional security, by identifying the merchant device as a legitimate recipient of the private information. In some examples, the secret key may be assigned to and stored by the merchant device. In other examples, the secret key may be generated by the merchant device for use only in the instant transaction.

The data device may evaluate the access token, the request for private information, and/or the secret key upon receipt, and if the evaluation is satisfactory, the data device may, in step 240, request confirmation from the user device that the private information sought by the merchant device may be sent. If, in step 245, the data device receives confirmation from the user device that the private information may be sent, the data device may send the private information to the merchant device via the secure back channel. If the user device denies confirmation, or does not provide confirmation within a prescribed period of time, the data device may not send the private information to the merchant device. In some examples, such as when the merchant device is recognized or provides additional identification (e.g., a secret key), data device may still request confirmation from the user device, but may proceed with sending the private information to the merchant device if a response denying confirmation is not received from the user device within a prescribed period of time. Upon receipt of confirmation, or when the time period for response denying confirmation has elapsed, the data device may transmit the private information to the merchant device in step 250.

Figure 3:
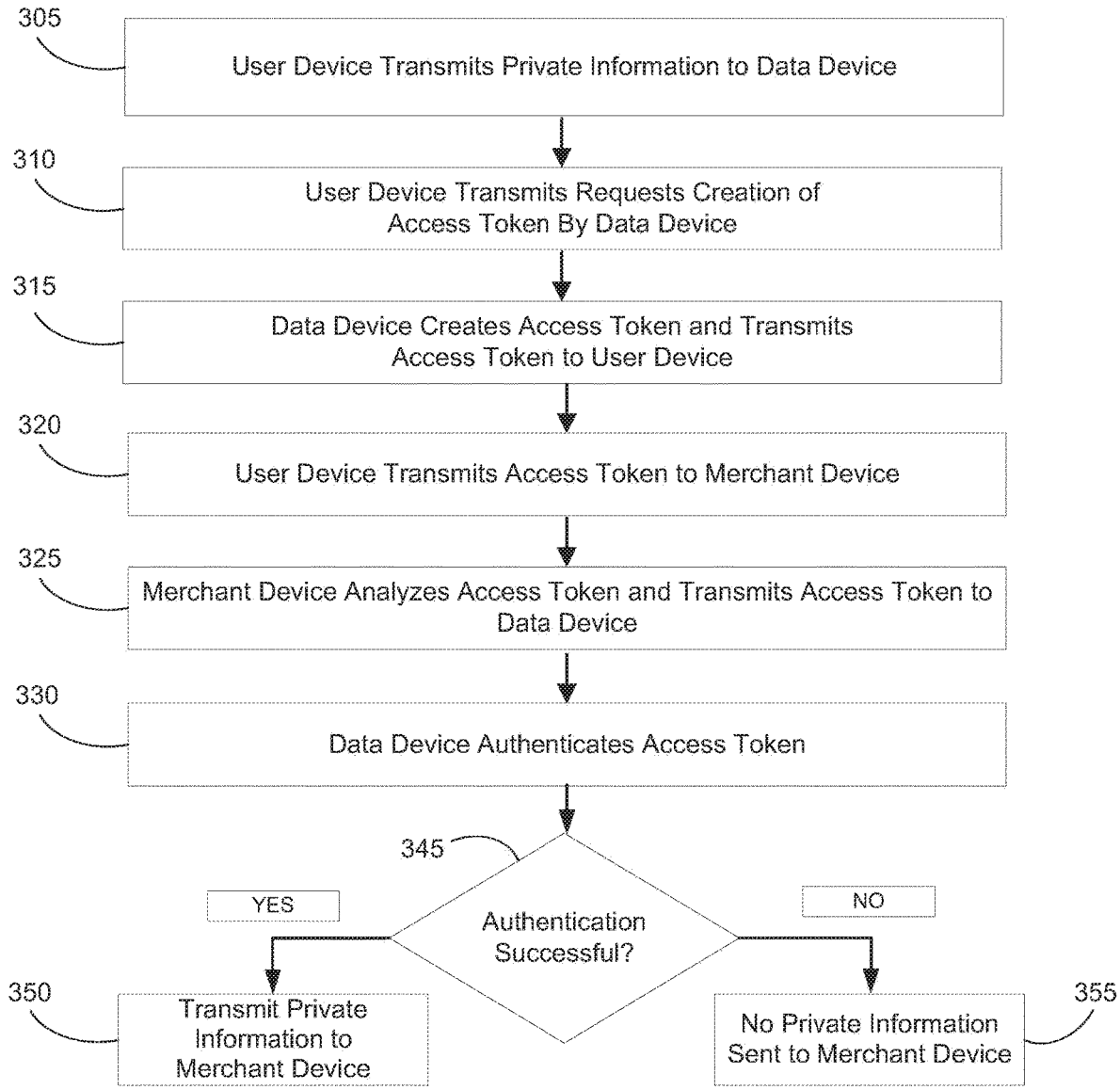
FIG. 3 is a flow chart illustrating a method of data delegation and control according to an example embodiment.

FIG. 3 is a flow chart illustrating a method of data delegation and control according to an example embodiment. FIG. 3 may reference the same or similar components as those illustrated in FIGS. 1 and 2, including a user device, a data device, a database, and a merchant device.

The method 300 may commence at block 305, where the user device transmits private information for storage in the data device. The private information may include personally-identifiable information, financial information, or any other information that may be sensitive or that the user desires to safeguard. The private information may be sent from the user device to a data device via a secure back channel. Upon receipt, the data device may store the private information in a database or other storage format, which may be located internally or externally to the data device.

In block 310, the user device may request that the data device create an access token. The user may request that the access token be a temporary token, such as a one-time use access token, a token limited to a certain number of uses, and/or a token limited to a specified time period, and/or a token limited to a particular merchant or third party such that only that merchant or third party is able to use the token to access private information of a user. In other examples, limitations may be placed on the token due to a data security policy, or based on the merchant device requesting private information.

Upon receipt of the user's request, in block 315, the data device may generate the access token. In some examples, the access token may be a random number. In other examples, the access token may be a tokenized version of the user's name, account number, user identifier, a portion of the private information, or a combination thereof. In other examples, the access token may be created without reference to the user or the private information, and instead may be generated with reference to the data holding entity (e.g., based on an identifier for the data holding entity or a sequence number) or may be randomly generated. Regardless of the manner of its creation, the access token may be associated with the user and/or the user's private information. In some examples, this association may be known only to the data device, and the association may not be apparent upon review of the access token by any other entity. However, other entities may be able to determine that the access token is associated with the data device and/or the data holding entity. Once generated the access token may be transmitted to the user device via a publicly accessible front channel or a secure back channel.

In block 320, the user device may transmit the access token to a merchant device in connection with a transaction. The user device may transmit the access token in lieu of sending private information to the merchant device, such that the no private information is transmitted by the user device to the merchant device.

Upon receipt of the access token, in block 325, the merchant device may analyze the token to determine if the token is associated with a data device or a data-holding entity. For example, the token may include code or set of numbers that identify a particular data device or data-holding entity. Upon determining that the access token is associated with the data device, the merchant device may transmit the access token to the data device. In some examples, this transmission may occur over a publicly accessible unsecure front channel. In other examples, a secure back channel can be used to transmit the access token from the merchant device to the data device.

In block 330, upon receipt of the access token from the merchant device, the data device may authenticate the access token. If, in block 345, the data device successfully authenticates the token, the method 300 may proceed to block 350. A successful authentication may establish that the access token was validly issued and identify the requested private information, and accordingly, the identified private information may be transmitted to the merchant device via a secure back channel in block 350.

Returning to block 345, if the authentication is unsuccessful, the method 300 may proceed to bloc 355 where no private information is sent to the merchant device. In some examples, a notification or message that the authentication of the access token was unsuccessful may be sent to the merchant device, however, in other examples no notification and/or message may be sent to the merchant device.

Figure 4:
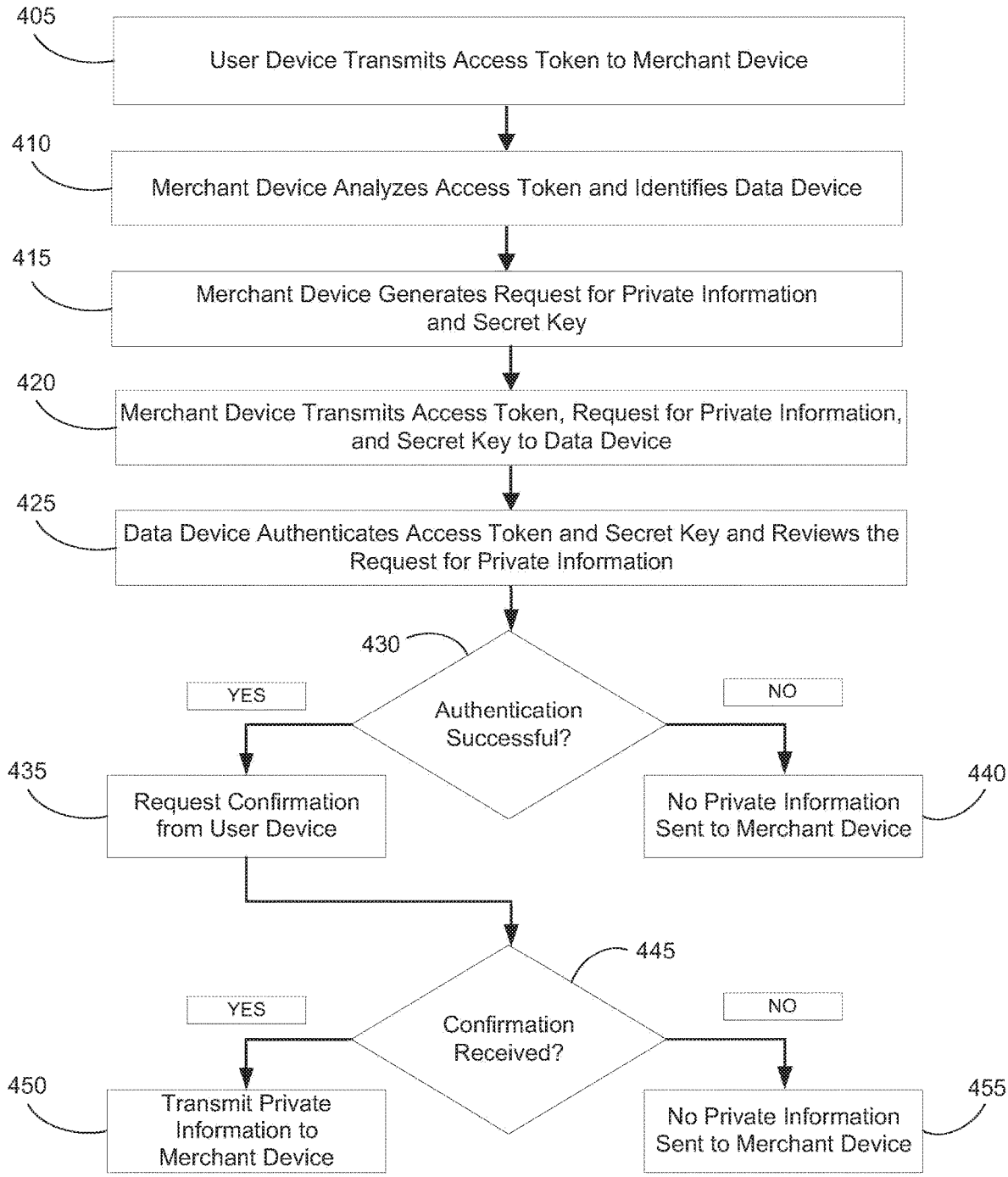
FIG. 4 is a flow chart illustrating a method of data delegation and control according to an example embodiment.

FIG. 4 is a flow chart illustrating a method of data delegation and control according to an example embodiment. FIG. 4 may reference the same or similar components as those illustrated in FIGS. 1-3, including a user device, a data device, a database, and a merchant device.

The method 400 may commence at block 405, where the user device may transmit an access token to the merchant device. In some examples, the access token may be requested from, generated by, and received from, a data device as described herein. The transmission of the access token from the user device to the data device may take place over a publicly accessible, unsecure channel.

In block 410, the merchant device may analyze the access token and determine the data device and/or data-holding entity that generated the access token. In some examples, the merchant device may also determine the type of information that the access token is associated with, e.g., the access token is associated with a street address, Social Security number, or a credit card number. Even in these examples, however, the analysis would not reveal to the merchant device the underlying private information, e.g., the street address, Social Security number, or credit card number.

In block 415, the merchant device may, based on the analysis of the access token, generate a request for private information. This request may identify the particular items of private information necessary for a transaction, for example. In some examples, the merchant device may generate a secret key using, for example, using symmetric encryption, a public/private key pair, message authentication code, or other cryptographic method. In other examples, the secret key may be assigned to and stored by the merchant device, instead of being generated. As an example, the secret key may comprise an OAuth client secret. The secret key may be transmitted, along with the access token and the request for private information, to the data device via a secure back channel.

In block 425, the data device may authenticate the access token and secret key, to determine their validity and whether the merchant device is a legitimate requestor of private information. In addition, the data device may review the request for private information to determine whether it is in possession of, or has access to, that private information. If not, the data device may notify the merchant device that the requested private information is not available.

If, in block 430, the authentication of the access token and the secret key is successful, the method may proceed to block 435 where the data device may request confirmation from the user device that the requested private information may be transmitted to the merchant device. In some examples, a notification and/or message may be sent as a pop-up notification on the user device or to an associated application installed on the user device. In other examples, the notification and/or message may be sent to an email address, phone number (via call or SMS/MMS message), or other contact information associated with the user or the user device.

If, in block 445, the user device responds with confirmation, the method 400 may proceed to block 450 and the requested private information may be transmitted from the data device to the merchant device via a secure back channel. If, in block 445, the user device responds by denying confirmation, then the method 400 may proceed to block 455 where no private information may be transmitted. In some examples, the data device may transmit private information to a trusted and/or previously-authenticated merchant device if a response denying confirmation is not received from the user device within a specified time period In other examples, such as when a merchant device is not trusted and/or previously authenticated, the data device may not transmit private information if affirmative confirmation is not received within a specified time period.

Figure 5:
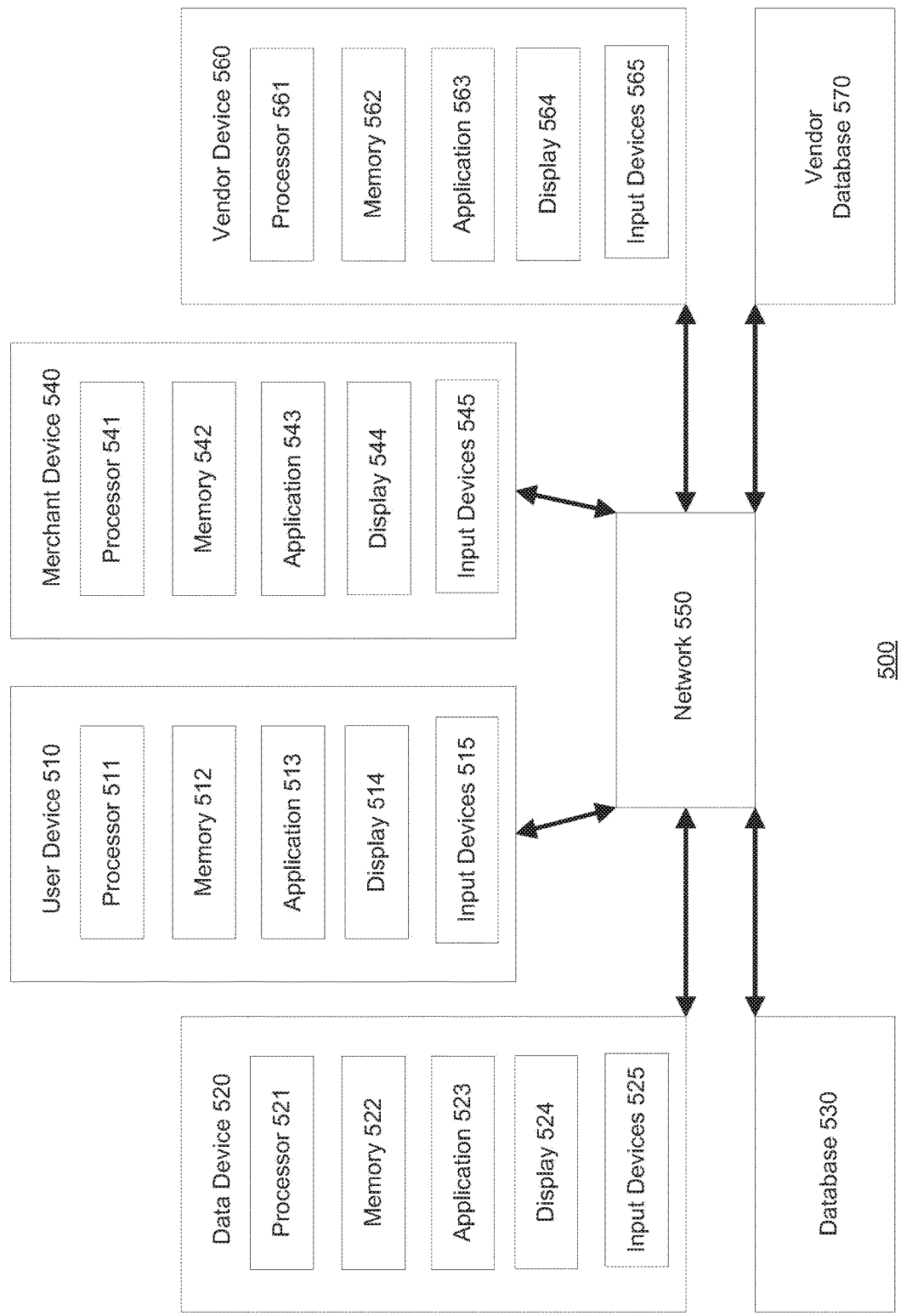
FIG. 5 is a diagram of a data delegation and control system according to an example embodiment.

FIG. 5 illustrates a data delegation and control system 500 according to an example embodiment. FIG. 5 may reference the same or similar components as those illustrated in FIGS. 1-4. Although FIG. 5 illustrates single instances of the components, system 500 may include any number of components.

As shown in FIG. 5, the user device 510 may comprise a processor 511, a memory 512, one or more applications 513, a display 514, and one or more input devices 515. The data device 520 may comprise a processor 521, a memory 522, one or more applications 523, a display 524, and one or more input devices 525. The merchant device 540 may comprise a processor 541, a memory 542, one or more applications 543, a display 544, and one or more input devices 545. FIG. 5 also illustrates a database 530 and a network 550. Each of these elements may be the same the respective elements described with reference to FIGS. 1-4.

FIG. 5 further illustrates a vendor device 560, which may be a network-enabled computer device. The vendor device 560 may comprise a processor 561, a memory 562, one or more applications 563, a display 564, and one or more input devices 565. The components of the vendor device 560 may function in the same manner as the components of the user, data, and merchant devices that have been previously described.

A vendor database 570 is also illustrated in FIG. 5. The vendor database 570 may be one or more databases configured to store date, including without limitation, private information. The database 570 may comprise a relational database, a non-relational database, or other database implementations, and any combination thereof, including a plurality of relational databases and non-relational databases. In some examples, the database 570 may comprise a desktop database, a mobile database, or an in-memory database. Further, the database 570 may be hosted internally by the vendor device 560 or may be hosted externally of the vendor device 560. The database 570 may be in data communication with the data device from its hosting location.

In some examples, the vendor device 560 may store certain private information associated with the user. This private information may be stored within the memory 562, within the vendor database 570, or a combination thereof. The amount of private information stored by the vendor device may be the same, less than, or greater than the private information stored by the data device 520. However, the situation may arise where the vendor device 560 seeks to request private information associated with the user from the data device 520.

For example, the vendor device 560 may be involved in a transaction that requires private information associated with the user that is not accessible to the vendor device. In connection with this transaction, the vendor device 560 may receive from the user device 510 an access token, which may have been generated by the data device 520 as described herein. In some examples, the access token may indicate that the vendor device 560 is in possession of certain private information and/or a certain type of private information associated with the user. In some examples, the access token may indicate that the vendor device 560 is in possession of some private information associated with the user, without specifying what private information or what type of private information. The vendor device 560 may transmit the access token to the data device 520 through a secure back channel.

The data device 520 may authenticate the access token to determine the validity of the access token and to identify the vendor device 560 as possessing certain private information associated with the user. To determine the legitimacy of the information request, the data device 520 may request that the vendor device 560 transmit, via a secure back channel, a portion of the private information associated with the user stored by the vendor device 560. For example, the data device 520 may request that the vendor device 560 transmit a street address, account number, or a birth date associated with the user. In some examples, the access token may indicate the particular type of private information stored by the vendor device 560 (e.g., a street address, an account number, a birth date). In response to the request made by the data device 520, the vendor device 560 may transmit, via a secure back channel, the requested portion of private information accessible to it.

The data device 520 may analyze the received portion of private information. For example, the data device 520 may compare the portion of private information to private information stored within the memory 522 and/or the database 530. This comparison may involve, without limitation, a direct textual comparison, natural language processing, the application of machine learning (e.g., gradient boosting machine, logistic regression, and neural networks) or other method of comparison. Based on the comparison, the data device 520 may generate a similarity score as a measure of the similarity of the portion of private information received from the vendor device 560 to the private information stored by the data device 520. If the similarity score meets or exceeds a specified threshold, the data device 520 may transmit the requested private information to the vendor device 560 via a secure back channel along with a message indicating that a successful comparison was made. If the similarity is below the specified threshold, the data device 520 may not send the private information and may instead send a message indicating that the comparison was unsuccessful. Receipt of an unsuccessful comparison message may prompt the vendor device 560 to pursue a second attempt.

In some examples, the threshold for evaluating the similarity score may be established by the user or by the data device 520. For example, a relatively low threshold may be established if the vendor device 560 has previously requested private information successfully (e.g., through a comparison of private information, through the use of a secret key) or if the vendor device 560 is known to the user within a trusted network of devices or vendors. In other examples, if those conditions do not apply, a relatively high threshold may be established for the vendor device 560. In other examples, the user may establish a high threshold out of a desire to increase data security.

Figure 6:
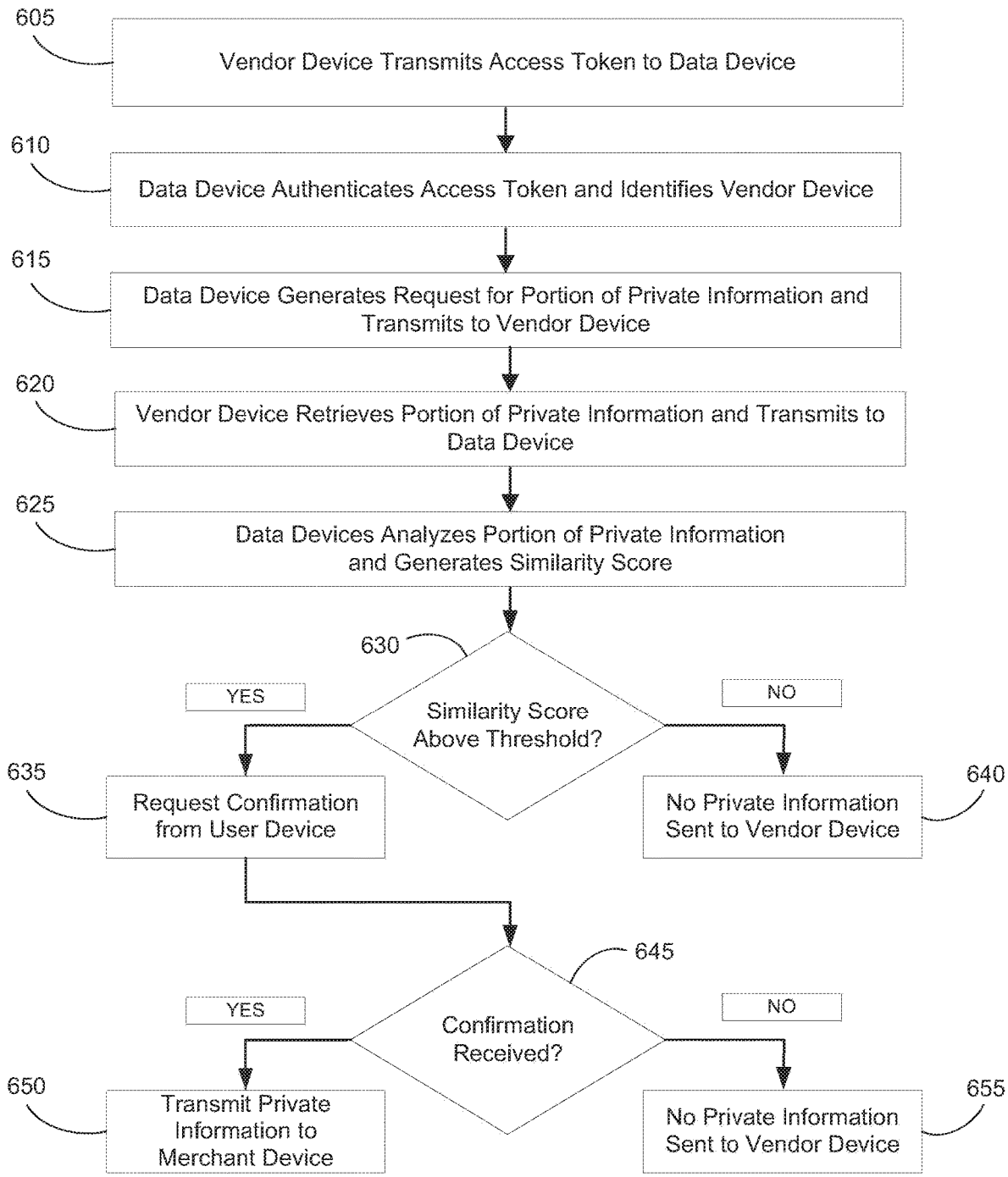
FIG. 6 is a flow chart illustrating a method of data delegation and control according to an example embodiment.

FIG. 6 is a flow chart illustrating a method of data delegation and control according to an example embodiment. FIG. 6 may reference the same or similar components as those illustrated in FIGS. 1-5, including a user device, a data device, one or more databases, a merchant device, and a vendor device.

The method 600 may commence at block 605, where a vendor device may establish a secure back channel and may transmit an access token to the data device. The access token may identify the vendor device and may indicate that the vendor device is in possession of private information relating to a user.

In block 610, the data device may authenticate the access token, identify the vendor device, and recognize that the vendor device is in possession of private information associated with the user. In block 615, the data device may generate a request for a portion of private information, and transmits that request to the vendor device via the secure back channel. In block 620, the vendor device may retrieve the requested portion of private information and transmits the requested private information to the data device via the secure back channel.

Upon receipt of the requested portion of private information, in block 625 the data device may analyze the portion of private information. The analysis may be a comparison of the received portion of private information to the private information stored by the data device. In some examples, the analysis may take the form of a direct comparison (e.g., for account numbers) and in other examples, the data device many employ natural language processing, machine learning, and/or other information analysis techniques. Based on this analysis, the data device may generate a similarity score as a measure of how the portion of private information received from the vendor device matches the private information stored by the data device. In block 630, this similarity score may be compared to a threshold score, which may be established, for example, as part of a data security policy implementing by the data holding entity associated with the data device or based on the user's preferences for sharing private information. If the similarity score exceeds the threshold, the method 600 may proceed to block 635, where a request for confirmation to share the private information may be sent to a user device associated with the user via a pop-up notification, or to a contact address (e.g., email address or telephone number). If the similarity score does not exceed the threshold, the method 600 may proceed to step 640 where no private information is sent to the vendor device. In some examples, a failure message may be sent by the data device to the vendor device to provide notice that no private information will be sent. In other examples, a notification and/or message of a successful comparison may be sent by the data device to the vendor device.

In block 645, if confirmation is received from the user device, the method 600 may proceed to block 650 and the data device may transmit the private information requested by the vendor device to the vendor device via a secure back channel. In some examples, since the vendor device has already established that it is in possession of some private information relating to the user, if a response denying confirmation is not received within a specified time period, the data device may transmit the requested private information to the vendor device. In other examples, an affirmative confirmation response must be received prior to the transmission of the private information.

Example embodiments of the present disclosure may provide for increased data security by limiting the instances where private information is transmitted. Further, in instances where private information may be transmitted, In some examples, the present disclosure refers to a transaction involving a merchant or vendor, and merchant devices or vendor devices, which may include, without limitation, retail merchants and vendors and associated devices. However, it is understood that the present disclosure is not limited thereto, and that the present disclosure includes any type of merchant, vendor, or other entity involving in activities where private information is required. Exemplary merchants and vendors include, without limitation, financial entities (e.g., banks, lenders, brokerages, insurers), governmental institutions, educational institutions, commercial and industrial entities such as manufacturers and retailers, any entity acting as an employer, and individual persons.

In some examples, the present disclosure refers to a transaction, which may include, without limitation, a financial transaction. However, it is understood that the present disclosure is not limited thereto, and that the present disclosure includes any type of transaction where private information is required. Exemplary transactions include, without limitation, financial transactions (e.g., deposits, withdrawals, and transfers of funds, purchases or sale of stocks, bonds, and options), identity verification, education transactions (e.g., enrollment, request or release of academic records, tuition payments), residency verification, account transactions (e.g., account opening, account actions, account closing), service transactions (e.g., initiating a service, paying for a service, terminating a service), and purchase transactions (initiating a purchase, authorizing a purchase, confirming a purchase, challenging a potentially unauthorized purchase, returning a purchase, and declining a purchase).

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

In this description, numerous specific details have been set forth. It is to be understood, however, that implementations of the disclosed technology may be practiced without these specific details. In other instances, well-known methods, structures and techniques have not been shown in detail in order not to obscure an understanding of this description. References to "some examples," "other examples," "one example," "an example," "various examples," "one embodiment," "an embodiment," "some embodiments," "example embodiment," "various embodiments," "one implementation," "an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrases "in one example," "in one embodiment," or "in one implementation" does not necessarily refer to the same example, embodiment, or implementation, although it may.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for data control, comprising:
 a data device comprising a processor and a memory; and
 a database containing private information, wherein the database is in data communication with the data device, wherein the data device:
  generates an access token associated with the private information,
  transmits the access token through a front channel,
  receives an information request through a secure back channel, the information request comprising the access token, a secret key, an identification of a first portion of private information, and a second portion of private information, and
  responsive to the information request, the data device:
   authenticates the access token and the secret key,
   retrieves a third portion of private information from the database based on the authentication of the access token and the secret key,
   compares the second portion of private information to the third portion of private information,
   generates a first similarity score based on the comparison of the second portion of private information to the third portion of private information, and
   upon determining that the first similarity score exceeds a first threshold:
    retrieves the first portion of private information from the database, and
    transmits the first portion of private information through the secure back channel.

2. The system for data control of claim 1, wherein the data device:
 transmits a notification to a user device indicating receipt of the information request, and
 transmits the first portion of private information upon receipt of an approval message from the user device.

3. The system for data control of claim 1, wherein the data device transmits the first portion of private information unless a disapproval message is received within a specified time period.

4. The system for data control of claim 1, wherein the data device applies a neural network to perform the comparison of the second portion of private information to the third portion of private information.

5. The system for data control of claim 1, wherein the first threshold is established based on a user preference received from a user associated with the data device.

6. The system for data control of claim 1, wherein the first threshold is established based on a previous comparison resulting in the generation of a previous similarity score for a previous information request.

7. The system for data control of claim 1, wherein:
 the information request is received from a requesting device, and
 the first threshold is established based on the membership of the requesting device in a trusted network.

8. The system for data control of claim 1, wherein:
 the information request is received from a requesting device, and
 the data device determines, based on the access token, whether the requesting device is in possession of any private information relating to the user.

9. The system for data control of claim 8, wherein the data device, upon a determination that the requesting device is in possession of private information, requests that the requesting device transmit a fourth portion of private information to the data device through the secure back channel.

10. The system for data control of claim 9, wherein, upon receipt of the fourth portion of private information, the data device:
 retrieves a fifth portion of private information from the database,
 compares the fifth portion of private information to the fourth portion of private information, and
 generates a second similarity score based on the comparison.

11. A method of data control by a data device comprising a processor and a memory, comprising:
 storing private information in the memory;
 generating an access token comprising tokenized data identifying the data device;
 transmitting, through a first front channel, the access token;
 receiving, through a first secure back channel, an information request comprising the access token; and
 responsive to the information request:
  authenticating the access token,
  transmitting, through the first secure back channel, a first portion of the private information based on the authentication of the access token,
  receiving through a second secure back channel, a request for a second portion of private information,
  receiving, through the second secure back channel, a third portion of private information,
  comparing the third portion of private information to a fourth portion of the private information,
  generating a first similarity score based on the comparison of the third portion of private information to the fourth portion of private information,
  determining that the first similarity score exceeds a first threshold, and
  upon determining that the first similarity score exceeds the first threshold, transmitting a share confirmation request.

12. The method of data control of claim 11, wherein the information request further comprises a secret key.

13. The method of data control of claim 12, wherein the secret key comprises an OAuth client secret.

14. The method of data control of claim 12, wherein the secret key is a single-use key.

15. The method of data control of claim 11, further comprising transmitting a confirmation request message upon authentication of the access token.

16. The method of data control of claim 11, wherein the share confirmation request includes a request for a biometric identifier.

17. A non-transitory computer-accessible medium having stored thereon computer-executable instructions for providing data control, wherein, when a computer arrangement executes the instructions, the computer arrangement comprising a processor in data communication with a database containing private information, the computer arrangement is configured to perform procedures comprising:

receiving, through a front channel, a request for an access token associated with the private information;

generating an access token, the access token comprising a tokenized identifier for the computer arrangement;

transmitting the access token through the front channel;

receiving, through a secure back channel, the access token, a secret key, and a request for a first portion of private information; and responsive to the request for the first portion of private information:

authenticating the access token and secret key, receiving, through the secure back channel, a second portion of private information, comparing the second portion of private information to a third portion of the private information, generating a similarity score based on the comparison, determining that the first similarity score exceeds a first threshold and upon determining that the first similarity score exceeds the threshold, transmitting the first portion of private information through the secure back channel.

18. The non-transitory computer-accessible medium of claim 17, wherein comparing the second portion of private information to the third portion of the private information comprises applying natural language processing to compare the second portion of private information to the third portion of the private information.

19. The non-transitory computer-accessible medium of claim 17, wherein comparing the second portion of private information to the third portion of the private information comprises a direct textual comparison of the second portion of private information to the third portion of the private information.

20. The non-transitory computer-accessible medium of claim 17, wherein the secure back channel comprises at least one selected from the group of a Hypertext Transfer Protocol (HTTP) secure socket layer (SSL) communication and a HTTP Secure (HTTPS) communication.

* * * * *